United States Patent
Charthad et al.

(10) Patent No.: US 10,177,606 B2
(45) Date of Patent: Jan. 8, 2019

(54) DYNAMIC RECONFIGURATION FOR MAXIMIZING THE OVERALL LINK EFFICIENCY OF ENERGY RECEIVERS IN A RELIABLE IMPLANTABLE SYSTEM

(71) Applicant: The Board of Trustees of the Leland Stanford Junior University, Palo Alto, CA (US)

(72) Inventors: Jayant Charthad, Stanford, CA (US); Marcus J. Weber, Palo Alto, CA (US); Mohammad Amin Arbabian, San Francisco, CA (US); Ting Chia Chang, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 298 days.

(21) Appl. No.: 15/282,417

(22) Filed: Sep. 30, 2016

(65) Prior Publication Data
US 2017/0117753 A1    Apr. 27, 2017

Related U.S. Application Data

(60) Provisional application No. 62/244,456, filed on Oct. 21, 2015.

(51) Int. Cl.
*H02J 50/15* (2016.01)
*A61B 5/01* (2006.01)
*A61B 5/07* (2006.01)
*A61B 5/04* (2006.01)
*A61B 5/03* (2006.01)
*A61B 5/145* (2006.01)
*A61B 5/00* (2006.01)
*A61N 1/372* (2006.01)
*A61N 1/378* (2006.01)
(Continued)

(52) U.S. Cl.
CPC ............... *H02J 50/15* (2016.02); *A61B 5/01* (2013.01); *A61B 5/036* (2013.01); *A61B 5/04001* (2013.01); *A61B 5/076* (2013.01); *A61B 5/14503* (2013.01); *A61B 5/4845* (2013.01); *A61N 1/3787* (2013.01); *A61N 1/37217* (2013.01); *A61B 2560/0219* (2013.01); *A61F 2007/126* (2013.01); *A61N 2005/0612* (2013.01); *H02J 7/025* (2013.01)

(58) Field of Classification Search
CPC ....................................................... H02J 50/15
See application file for complete search history.

(56) References Cited

U.S. PATENT DOCUMENTS 5,733,313 A    3/1998    Barreras et al.
8,082,041 B1    12/2011    Radziemski
(Continued)

FOREIGN PATENT DOCUMENTS

WO    WO2015/196290    12/2015

*Primary Examiner* — Fritz M Fleming
(74) *Attorney, Agent, or Firm* — Lumen Patent Firm

(57) ABSTRACT

Efficient power transmission from an acoustic transmitter to an electrical load on an implanted device is provided using a control system that at least varies the transmitted acoustic frequency. Varying the transmitted frequency can change the electrical impedance of the acoustic transducer in the receiver that receives power from the transmitter. This ability to vary the transducer impedance can be used to optimize power delivery to the load.

22 Claims, 14 Drawing Sheets

(51) Int. Cl.
*H02J 7/02* (2016.01)
*A61F 7/12* (2006.01)
*A61N 5/06* (2006.01)

(56) References Cited

U.S. PATENT DOCUMENTS

| | | | |
|---|---|---|---|
| 8,634,928 B1 | 1/2014 | O'Driscoll et al. | |
| 9,095,729 B2 | 8/2015 | John | |
| 9,525,311 B2 * | 12/2016 | Menegoli | H02J 50/15 |
| 2008/0077184 A1 | 3/2008 | Denker et al. | |
| 2010/0280568 A1 | 11/2010 | Bulkes et al. | |
| 2011/0285349 A1 | 11/2011 | Widmer et al. | |
| 2014/0336474 A1 | 11/2014 | Arbabian et al. | |
| 2015/0091706 A1 | 4/2015 | Chemishkian | |
| 2015/0280444 A1 | 10/2015 | Smith et al. | |
| 2016/0059012 A1 | 3/2016 | Adamson et al. | |
| 2017/0201130 A1 * | 7/2017 | Park | H02J 50/15 |

* cited by examiner

DYNAMIC RECONFIGURATION FOR MAXIMIZING THE OVERALL LINK EFFICIENCY OF ENERGY RECEIVERS IN A RELIABLE IMPLANTABLE SYSTEM

CROSS REFERENCE TO RELATED APPLICATIONS

This application claims the benefit of U.S. provisional patent application 62/244,456, filed on Oct. 21, 2015, and hereby incorporated by reference in its entirety.

FIELD OF THE INVENTION

This invention relates to acoustically powered implanted devices.

BACKGROUND

Implanted medical devices are of increasing interest for a wide variety of medical applications. Providing power to implanted medical devices has been performed in various ways. For example, power can be provided to implanted medical devices using RF (radio frequency) radiation or inductive coupling. Another approach is ultrasonic power transmission, which is expected to provide better performance than electromagnetic power transmission for implanted devices in some cases. US 2014/0336474 provides examples of ultrasonic power transmission, and is hereby incorporated by reference in its entirety.

However, the design considerations for efficient power transfer in an ultrasonic power transmission system are substantially different from those that arise in connection with electromagnetic power transmission for implanted devices. Therefore, design approaches suitable for providing efficient electromagnetic power transmission to implanted devices aren't applicable to ultrasonically powered implanted devices. Accordingly, it would be an advance in the art to provide improved ultrasonic powering of implanted devices.

SUMMARY

The main idea of this work is to provide efficient power transmission from an acoustic transmitter to an electrical load on an implanted device using a control system that at least varies the transmitted acoustic frequency. This unusual feature of varying the transmitted frequency can have many effects on system performance, but the effect of greatest interest is its influence on the electrical impedance of the acoustic transducer in the receiver that receives power from the transmitter. This ability to vary the transducer impedance can be used to optimize power delivery to the load via impedance matching, where it is understood that the impedances being matched may depend on power or other operating conditions of the system (i.e., the overall system is typically nonlinear).

In most cases, the real part of the transducer impedance will roughly match the real part of the impedance looking into the matching network, while the imaginary part of the transducer impedance is positive (i.e., inductive) and can be compensated using an adaptive and purely capacitive matching network. This advantageously avoids the need to use inductors as separate components for impedance matching. Such avoidance of discrete inductors is beneficial because in the frequency range of interest, the physical size of typically required discrete inductors is too large for use in miniaturized applications like implanted medical devices.

To better appreciate this work, it is helpful to state the problem to be solved more explicitly, with reference to the example of FIG. 2. The total efficiency of the link is a product of the efficiencies of all the sub-blocks of the system, as shown in FIG. 2. $\eta_{source}$ includes the efficiency and effective aperture of the Tx (transmitter). $\eta_{medium}$ includes channel losses, including but not limited to: propagation losses, diffraction, attenuation, reflections, impedance mismatch of mediums, changes in range, misalignment and rotation. $\eta_{rec}$ is the efficiency and effective aperture of the Rx (receiver). $\eta_{match}$ refers to the impedance match efficiency between the power receiver and the matching network as well as any losses in the matching network itself. $\eta_{circuit}$ includes the efficiency of the power recovery circuit. It can be noted that maximum overall link efficiency will be obtained by tweaking each of these individual efficiencies, and is not necessarily achieved at the maximum of any or all of these individual efficiencies. During the operation of a wireless power system, several factors may change or affect the individual components of the system which can produce a degradation in efficiency:

1) The Tx properties including efficiency, impedance and beam pattern could change over time, potentially due to any environmental variations, physiological state, positional drift or rotation, or any objects surrounding the Tx.
2) The medium between the Tx and the Rx can be perturbed, for instance: the distance between the Tx and Rx can change, objects may enter the medium, the properties of the medium could change due to temperature, pressure variations or physiological state, etc.
3) Like the Tx, the Rx properties including efficiency, impedance and aperture could also change over time, potentially due to any environmental variations, physiological state, positional drift or rotation, or any objects surrounding the Rx.
4) The properties of the matching network and the power recovery circuits could change due to environmental factors such as humidity and temperature variations.
5) The electrical load is a function of the desired tasks being performed, which can fundamentally change due to different applications, as well as over time from different operation modes in a system.

If the system is originally operating in a desired state, these aberrations will lead to drift from that original intended operating point over time. This will lead to a sub-optimal operation of the system. The purpose of the control system as described herein is to address this problem.

DETAILED DESCRIPTION

A) General Principles

Figure 1:
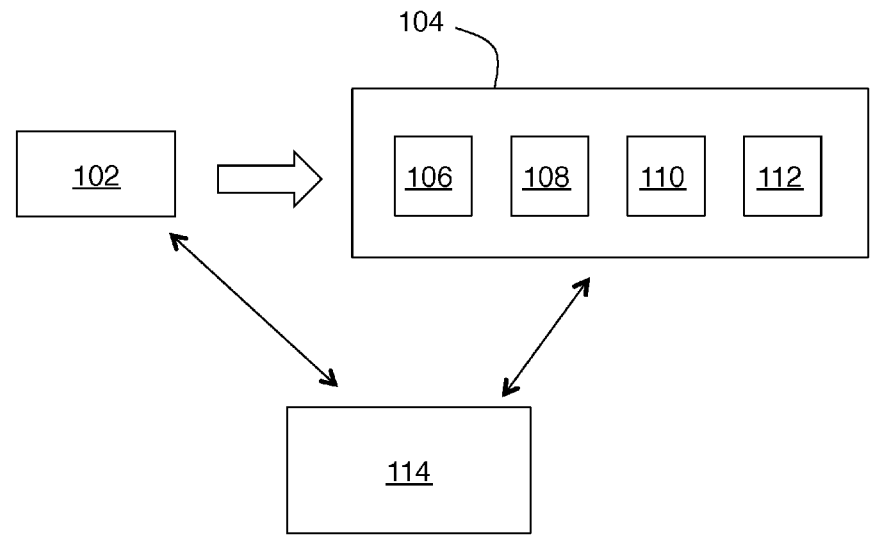
FIG. 1 is a block diagram of an embodiment of the invention.

As indicated above, the main idea is a control system for ultrasonic power transmission to an implanted device having acoustic frequency as one of the variables under control. An exemplary embodiment of the invention is shown on FIG. 1. This example is a system for providing power to an implanted receiver. It includes an acoustic transmitter 102 configured to provide acoustic radiation having an acoustic frequency f, a receiver unit 104 configured to be implanted into a biological subject, and a system controller 114.

Receiver unit 104 is configured to receive the acoustic radiation and to be powered by the acoustic radiation. Receiver unit 104 includes an acoustic transducer 106 configured to receive the acoustic radiation and to provide an input electrical AC signal, an adaptively reconfigurable electrical impedance matching network 108 configured to receive the input electrical AC signal and to provide an output electrical AC signal, a power recovery circuit 110 and an electrical load 112. The electrical impedance matching network 108 is capacitive without including any inductors. The power recovery circuit 110 is configured to receive the output electrical AC signal and to provide DC power to the electrical load 112.

System controller 114 is configured to a) alter one or more controlled system parameters including the acoustic frequency f, and b) alter a configuration of the adaptively reconfigurable electrical impedance matching network; responsive to changes in one or more system variables to control power delivery from the acoustic transmitter to the electrical load. Practice of the invention does not depend on where the components of the system controller are located. System controller components can be on a separate unit (e.g., 114 on FIG. 1), and/or can be included on transmitter 102 and/or can be included in receiver unit 104 in any combination. The initial operating point of the system could have been designed with specific properties and then the system could have calibrated itself using sensing and system reconfiguration at startup and during operation.

As indicated above, it is preferred for the system to be operating at or near a frequency range where the transducer reactance is positive. Here a "positive reactance band" of an acoustic transducer is any frequency band in which the acoustic transducer provides a positive reactance (i.e., has a positive imaginary part of its electrical impedance). The "inductive band" of an acoustic transducer is any positive reactance band of the acoustic transducer+/−20% in frequency. More specifically, if the positive reactance band is $f_1 \le f \le f_2$, the corresponding inductive band is $0.8 f_1 \le f \le 1.2 f_2$. Preferably the system operates in the inductive band as defined above.

Figure 2:
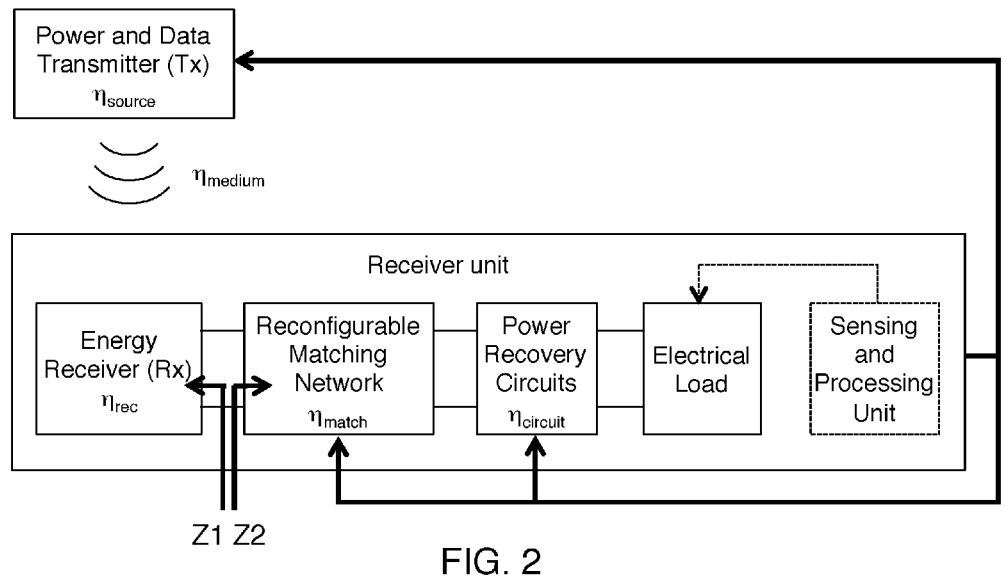
FIG. 2 is a more specific exemplary block diagram of an embodiment of the invention.

In preferred embodiments, the acoustic frequency is controlled by the system controller such that the impedance of the acoustic transducer (e.g., Z1 on FIG. 2) is tuned to impedance match the impedance as seen at the input of the adaptively reconfigurable electrical impedance matching network for an electrical load (e.g., Z2 on FIG. 2). "Impedance match" as referred to herein denotes an exact impedance match or an approximate impedance match to within 50% (i.e. considering the reflected power to be within 50% of available power). More specifically, two complex impedances Z1 and Z2 are matched if Z1=Z2* (where * denotes complex conjugate) or if $|Z1-Z2*|^2 < 0.5|Z1+Z2|^2$. This definition is typically applied to linear circuits, but in many cases, especially with non-linear power conditioning circuits, equivalent impedance can be derived while taking into account the non-linearity. In some cases the equivalent impedance can also be time-varying, especially when energy storage components are involved in the system. In certain scenarios, due to limitations of the transducer, matching network, and power recovery circuits, an exact impedance match may not be achievable; in those cases, impedance match refers to maximum possible impedance match that can be obtained or within 50% of the maximum possible impedance match.

In preferred embodiments, the acoustic frequency is controlled by the system controller such that the end to end power transmission efficiency from transmitter to load is locally maximal. More specifically, perturbations to the system operating point will cause the controller to seek a frequency that provides increased or maintained efficiency relative to the pre-perturbation operating point. System control according to this principle is expected to inherently result, in most cases, in impedance matching and operating with the acoustic transducer in its inductive band as described above.

The acoustic transmitter can be configured to provide continuous acoustic radiation. Here the acoustic frequency is varied continuously by the system controller. Alternatively, the acoustic transmitter can be configured to provide pulsed acoustic radiation. Here the acoustic frequency can be varied from pulse to pulse and/or varied within pulses by the system controller.

The controlled system parameters can be parameters including but not limited to: power from the acoustic transmitter, beam pattern of the acoustic radiation, phase of the acoustic radiation, pulse duration of the acoustic radiation, and duty cycle of the acoustic radiation.

The properties of the Tx such as its efficiency, transmission power, impedance, and beam pattern can be controlled by system parameters such as operating frequency, input power level, or time delay between elements on the Tx. For instance, if the implant drifts or rotates in any direction, the Tx can be adaptively beam-formed in order to maintain maximum efficiency. Additionally, the transmitted power could also be increased if the Rx platform rotates or drifts, in order to support a given load power. The transmitted power could also be increased if the load requirement increases or if the system detects a low available power at the Rx due to any variations. Similarly, the transmitted power could be reduced and operating frequency can be changed when the load requirement drops or the system detects a greater than required available power at the Rx due to any variations. An adaptive matching network and driving circuits can be added to the Tx in order maximize the system efficiency. Certain link aberrations may also require changing the phase of the Tx output waveform, changing the ON time of the Tx, or changing the duty cycle of the Tx output waveform. For instance, the Tx can provide power in bursts of energy with an adaptable duty cycle, rather than continuously providing power for a particular duration.

The system variables being monitored can include but are not limited to: load impedance, acoustic transmitter efficiency, acoustic transmitter impedance, acoustic transmitter beam pattern, distance between the acoustic transmitter and the receiver unit, transmission efficiency between the acoustic transmitter and the receiver unit, receiver unit efficiency, receiver unit impedance, receiver unit aperture, changes in parameters of the power recovery circuit, and changes in parameters of the adaptively reconfigurable electrical impedance matching network.

The electrical load can provide various functions, including but not limited to: electrical stimulation, optical stimulation, acoustic stimulation, neural recording, temperature sensing, pressure sensing, drug sensing, impedance sensing, detecting biological species, heating, and data communication. The electrical load can be an energy storage device, such as a battery or a capacitor.

For charging a rechargeable battery or a storage capacitor on the Rx, the transmitted power profile can be shaped such that power delivery efficiency is maximized to reach a desired voltage level on the battery or capacitor. By adjusting the transmitted power profile from Tx, available power from Rx can thus be controlled continuously. To efficiently charge an energy storage element to a certain voltage with a given time, a ramp profile of the transmitted power of Tx is desired. The voltage level of the battery or capacitor can be sensed and communicated back to the Tx unit. The operation of the Tx and Rx, matching network, and power recovery circuit can be adapted to optimize the total link efficiency.

Electrical loads determine the operating condition of the implant. The implant may be equipped with several functionalities, such as electrical or optical stimulation, neural recording, temperature and pressure sensing, and data communication, which require different power levels. For certain embodiments, system performs load interrogation and dynamic system calibration for overall maximum power transfer efficiency for electrical stimulation implants. The implant can continuously or periodically monitor the impedance of the tissue between electrodes and adjust the system parameters including, but not limited to, the power transfer frequency.

In some cases the electrical load is fixed rather than dynamic. System control as described herein can still be performed, where the system can be regarded as responding to perturbations in system operation such as change of environment or physiological state other than changes in the load by altering at least the acoustic frequency to optimize power transfer to the load.

The system controller can have sensors including but not limited to: load power sensor, load voltage sensor, load current sensor, output electrical AC signal voltage sensor, transducer output impedance sensor, transducer output voltage sensor, transducer output current sensor, receiver unit temperature sensor, and acoustic transmitter temperature sensor. For example, if the load on FIG. 2 is a battery, a load voltage sensor can be used to monitor how charged or discharged the battery is (i.e. the voltage level of the battery).

In order to determine desired system parameters and internal block parameters, and to know when they should be varied, sensing of key system metrics is preferably performed. For instance, monitoring the load power, output voltage or current, input voltage of the power recovery circuit, receiver impedance or voltage, the Tx voltage are just some of the metrics which can be useful for characterizing the system. Once desired system parameters are determined, then the entire system can be reconfigured Examples of sensors are capacitor voltage or load current sensor, and comparator comparing to fixed/re-configurable thresholds. In some embodiments, this block will also include ADC (analog to digital converter), FSM (finite state machine) etc.

The power recovery circuit can also be adaptively reconfigurable responsive to changes in the one or more system parameters. FIG. 2 shows an example of this configuration. Different implementations of the power recovery circuits include only rectifier, rectifier with addition of charge pump for different voltage/current ratio, rectifier with voltage regulator for getting a regulated voltage, and so on. Power recovery circuit can also include one or more storage elements or no storage element. In addition, more electronics can be included in the power recovery circuit in order to adjust the effective impedance to further improve the matching efficiency and thus overall efficiency.

Other reconfigurable parameters of the system include but are not limited to input power to the Tx, Tx beam forming pattern, matching network topology and components, voltage and current transformation ratios in the power recovery circuit, internal clock frequencies, and voltage and current supplies.

Figure 3A:
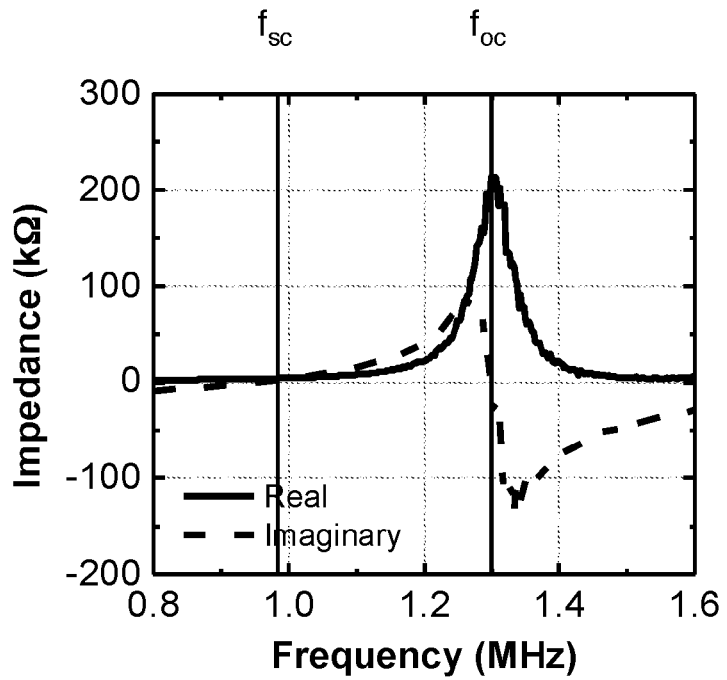
FIG. 3A shows the frequency dependence of the impedance of an exemplary acoustic transducer.
Figure 3B:
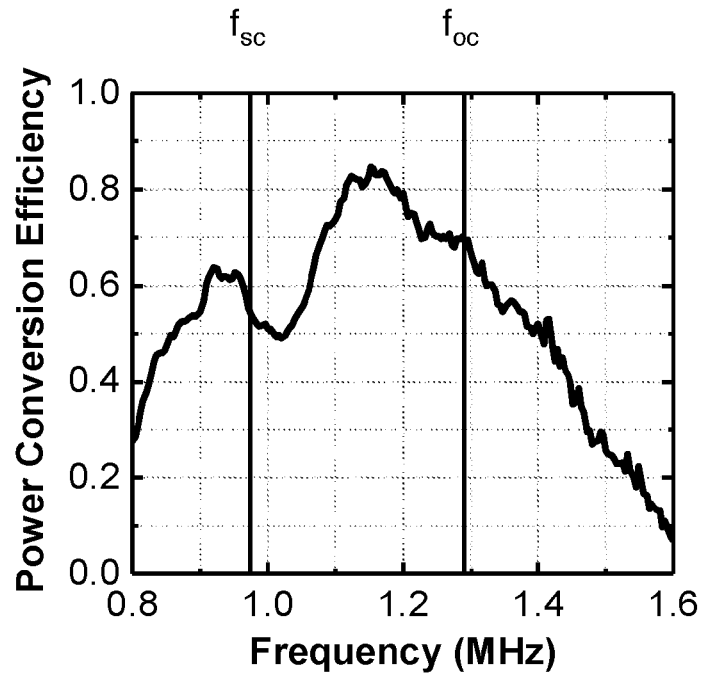
FIG. 3B shows the power conversion efficiency of the exemplary acoustic transducer of FIG. 3A.

The reconfigurable parameters are usually frequency dependent; therefore, one can optimize system efficiency by choosing an optimal frequency for different operating conditions. Most wireless power transfer links operate at the resonance frequency of the Tx and Rx devices; however, with adaptive matching and system reconfiguration this is not necessary and will often result in non-optimal efficiency, especially in the presence of link aberrations. For example, both the impedance of Tx and Rx can be changed with frequency. Similarly, efficiency and effective aperture of Rx can also be controlled by frequency. As shown in FIGS. 3A-B, the power conversion efficiency ($\eta_{rec}$) and the impedance of an example ultrasonic transducer used in ultrasonically powered implants is a function of frequency. $\eta_{match}$ can be optimized by operating at optimal frequency for different power consumed by electrical loads.

Figure 4:
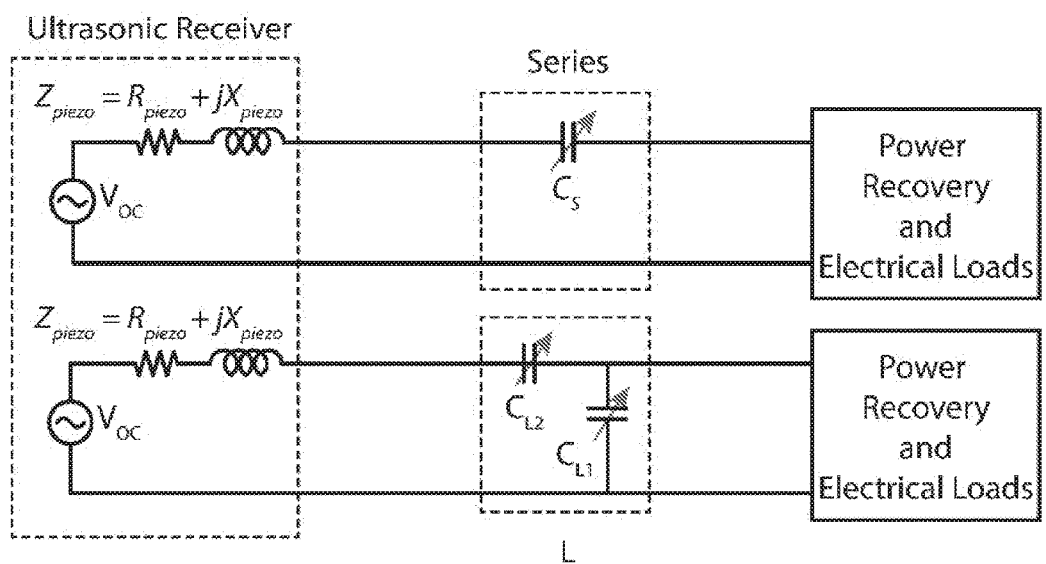
FIG. 4 shows two examples of matching networks.

Since the effective impedance of reconfigurable matching network along with the power recovery circuit is dependent on frequency, power level, and also on the input voltage or current, if changes in the system parameters are performed, the reconfigurable matching network should be adjusted in order to maximize the power delivered to the load by efficiently interfacing the power receiver to the power recovery circuit. The matching network can be reconfigured using several switches and passive and/or active components (inductors, capacitors, transmission lines, baluns or transformers, switched capacitor circuits or programmable on-chip capacitor array) for enabling a power match to the receiver. Examples of reconfigurable matching networks for ultrasonically powered medical implants are shown on FIG. 4. Here, the capacitance is adaptively changed based on different electrical load power.

In certain scenarios, the system controller adjusts the system parameters including the power transfer frequency through a real-time closed-loop control. In certain other cases, where the changes in the load or the system parameters are predictable (e.g., during an initialization prior to beginning closed loop control), the system controller changes the system parameters, including the power transfer frequency, in a pre-determined order. Here the system variables driving the control are predetermined (e.g., a programmed initialization sequence).

Figure 5:
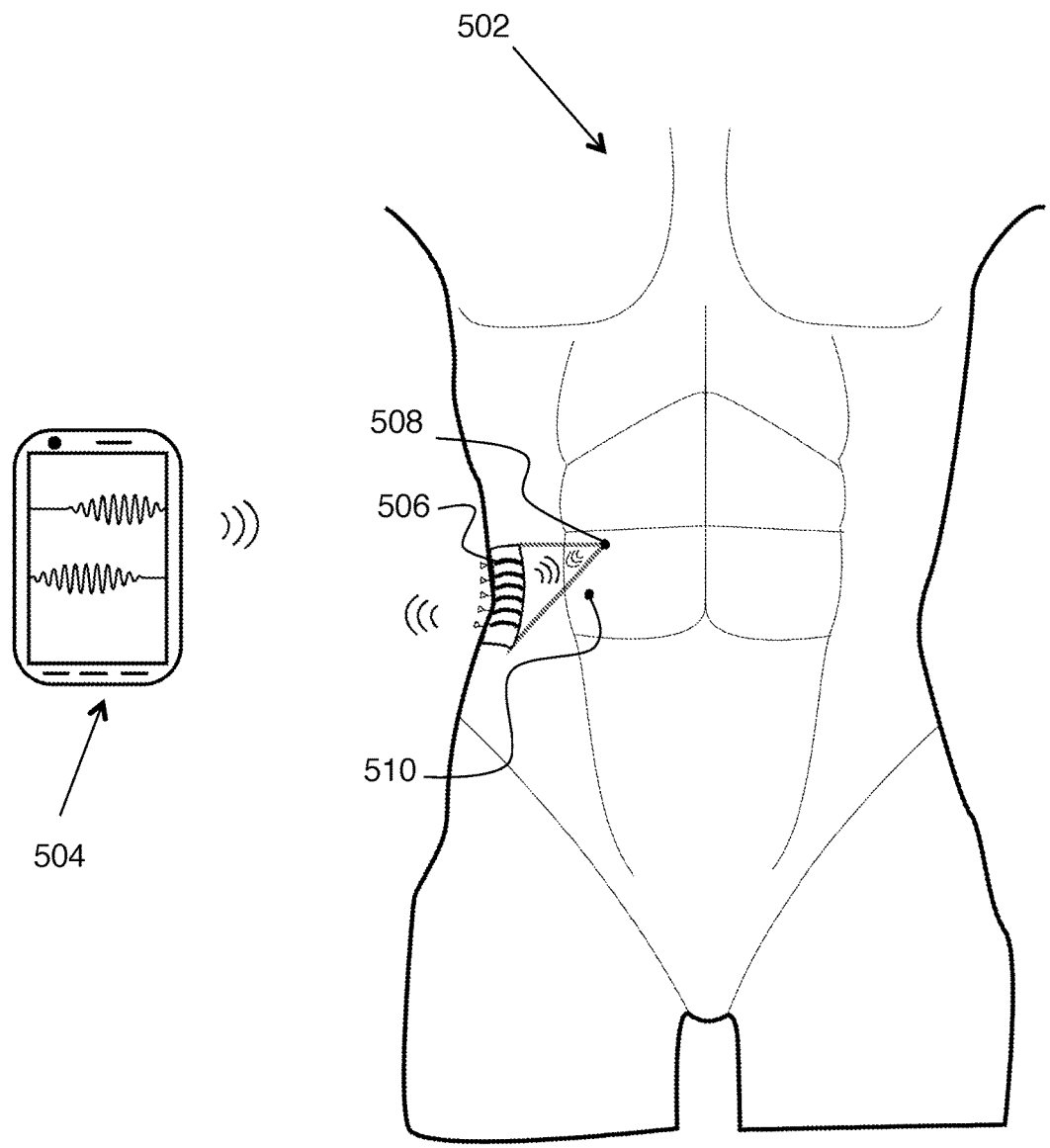
FIG. 5 is a diagram showing an embodiment of the invention having a wearable acoustic transmitter in communication with a mobile device.

FIG. 5 shows an exemplary embodiment where the acoustic transmitter 506 is configured to be wearable while it is acoustically powering implanted receiver units 508 and/or 510. Here receiver units 508 and 510 are implanted in the body 502 of a user. Preferably, acoustic transmitter 506 is configured to be in communication with a mobile device 504. This can provide a convenient way for the user to be informed of system operation, status reports, diagnostic results, etc.

For an ultrasound powered implantable system, the external ultrasound power transmitting and data receiving unit can be a wearable and/or flexible device contacted to the skin; one example is a band aid device. The external unit itself can be connected to a base station, which can be a mobile device (e.g. phone), through RF wireless technology or using wire. Closed loop processing can take place between implant, wearable ultrasonic powering unit, or base station, or any combination of these.

Figure 6:
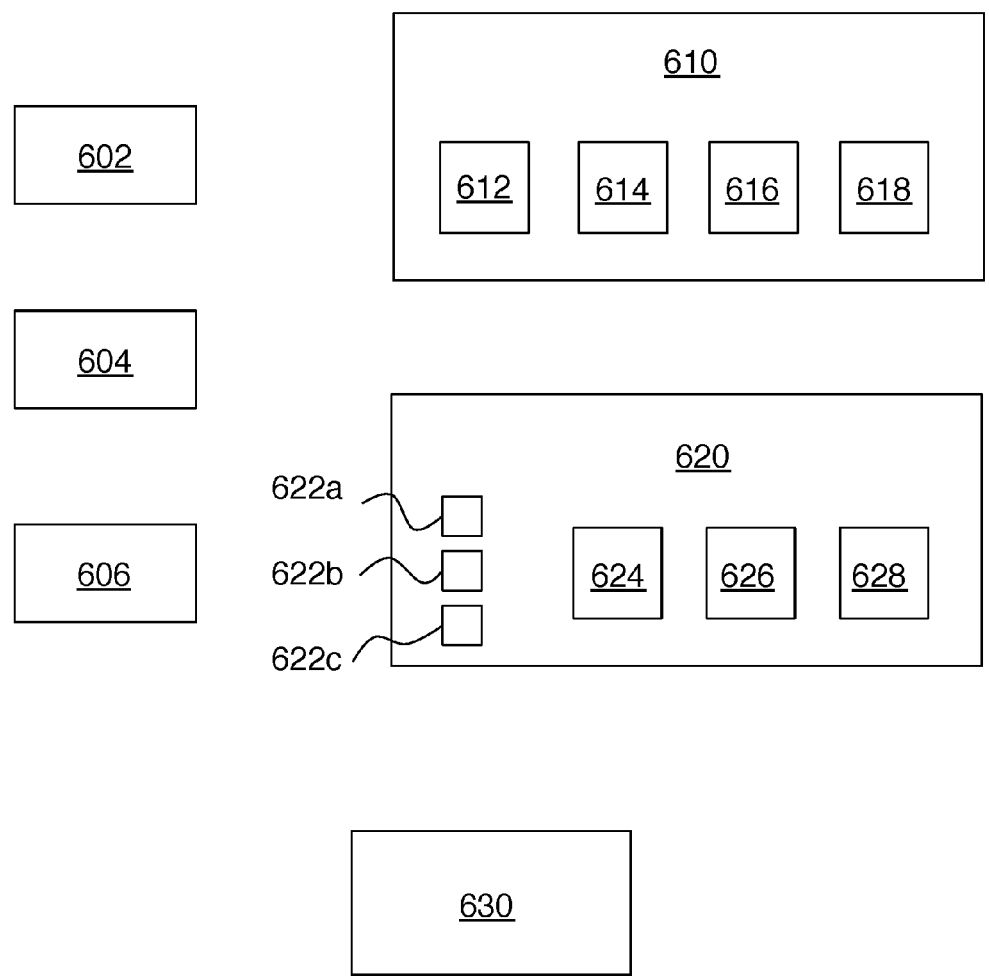
FIG. 6 shows an exemplary embodiment of the invention having multiple transmitters and receivers.

Systems according to the above-described principles can include multiple transmitters, multiple receiver units, and/or multiple transducers on a receiver unit, in any combination. FIG. 6 shows an example having transmitters 602, 604, and 606, receiver units 610 and 620, and system controller 630. Receiver unit 610 includes transducer 612, matching network 614, power conversion circuit 616 and load 618. Receiver unit 620 includes transducers 622a, 622b and 622c, matching network 624, power conversion circuit 626 and load 628.

Receiver unit 620 can be regarded as including two auxiliary acoustic transducers (e.g., 622b and 622c) in addition to acoustic transducer 622a. An output of acoustic transducer (622a) and outputs of the auxiliary acoustic transducers (622b and 622c) can be combined and provided to the electrical load 620. This combining can be done coherently or incoherently. In this case, the controlled system parameters can further include a combining configuration of the acoustic transducer and the one or more auxiliary acoustic transducers.

Figure 7:
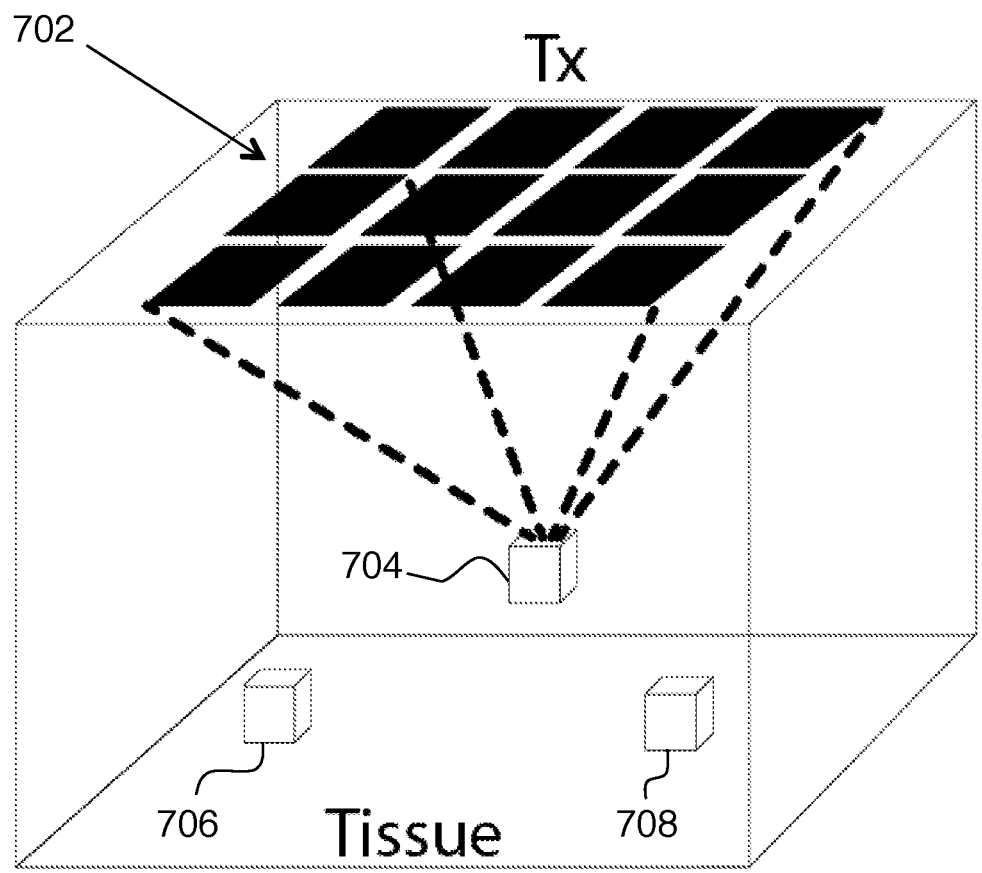
FIG. 7 is a further example of a multi-transmitter configuration.

Other functions can also be provided with multi-Tx and/or multi-Rx configurations. The system controller can be configured to provide location tracking of the receiver unit combined with beam forming of the acoustic radiation according to the tracked location of the receiver unit. FIG. 7 shows an example of this, where a Tx array 702 provides beam forming that allows selection between multiple implants 704, 706, 708, tracking motion of one or all of these implants, and/or simultaneous powering of the implants via transmission beam forming.

Adaptive beam-forming on the Tx can be used to individually address and power one or multiple receiver platforms. One method for adaptive beam-forming is to first image the surroundings using the Tx and determine the coordinates and orientation of each receiver platform. These coordinates and orientation information can be stored in the memory of either the Tx or the receiver platform or both. Further, this data can be matched against the unique address or code of each receiver platform and stored in the memory. This operation of imaging the surroundings and storing the relevant data can be performed periodically. Periodic updating is preferred due to reasons discussed above, including, but not limited to: changes in environmental conditions of the link, objects surrounding the link, misalignment and/or rotation of the receiver platform, changes in the properties of the electronic circuits, change in the electrical load, etc. Further, the receiver platform can communicate its unique address, code or other information to the Tx by data transmission.

Time multiplexing can be used by the Tx to power-up and communicate with the receiver platforms. In certain embodiments, the Tx can perform multi-lobe beam-forming to simultaneously power-up and/or communicate with multiple receiver platforms. The Tx could also use multiple frequencies to simultaneously power-up and/or communicate with multiple receiver platforms. In such embodiments, the link between each Tx and receiver platforms can be dynamically reconfigured for optimizing efficiency separately for each link.

Multiple Tx devices can be employed to power-up a single or multiple receiver platform devices to offer more flexibility for beam-forming, as well as to enable sufficient power transfer without exceeding any regulations. A Tx may be composed of a single element or a multi-element array.

In preferred embodiments, the receiver unit includes a back-side structure having low acoustic impedance (i.e., acoustic impedance of 10 Mrayl or less, more preferably 2

Figure 11:
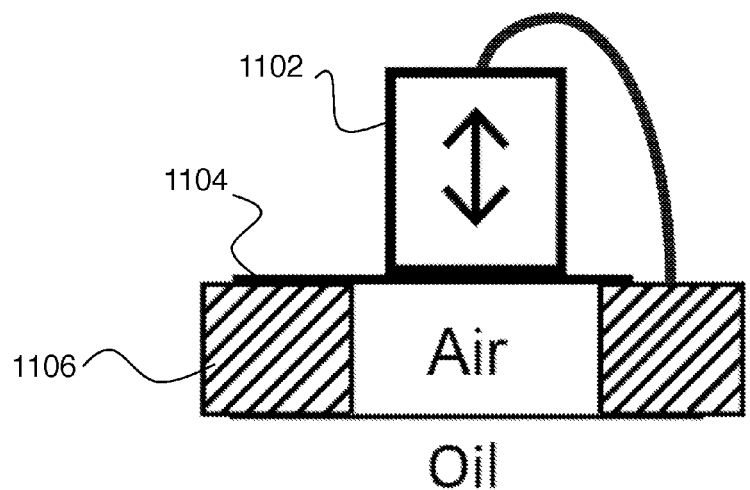
FIG. 11 is a diagram of an exemplary ultrasonic receiver package.

Mrayl or less. FIG. 11 shows an example, where the low acoustic impedance is provided by a back side air gap. Here "Acoustic impedance" is specific acoustic impedance having SI units (Pa s/m) also denoted as Rayl.

B) Experimental Demonstration

B1) Introduction

It has been proposed that implantable medical devices (IMDs) employing neuromodulation therapies, or "electroceuticals," may supplant drugs as the primary treatment for many neurological disorders. Unlike drugs which freely diffuse about the body, neuromodulation therapies are more targeted, allowing for the mitigation of unwanted side-effects. There are already many neuromodulation devices on the market or in development to treat disorders like Parkinson's and chronic pain; however, some of them are large, invasive, and prone to causing infection. In order to alleviate these issues, researchers are attempting to shrink the implants down to millimeter or sub-mm sizes and replace bulky batteries with reliable and highly efficient wireless power links. Most of these researchers have focused on RF or inductive powering, but as we have described in previous studies, ultrasonic power delivery has several key advantages over conventional RF and inductive powering when shrinking down to the mm-scale. Namely, ultrasound undergoes relatively small propagation losses through tissue (~1 dB·MHz/cm) and has a high FDA allowed time-averaged intensity (7.2 mW/mm$^2$), making it ideal for efficient power transmission at great depths (>5 cm). Additionally, ultrasound has small wavelengths in tissue (e.g. 1.5 mm at 1 MHz) allowing for superior energy focusing down to mm-spots, as well as more efficient energy recovery from a ultrasonic receiver.

Current and future IMDs may be equipped with several functionalities, such as electrical or optical stimulation, neural recording, and temperature and pressure sensing within one module—these functions require a large range of average implant load ($P_{load}$) typically ranging from 10 μW to 1 mW. In addition, next-generation IMDs will be programmable with duty-cycled operation and different functional modes, leading to dynamically varying $P_{load}$ for an individual IMD. Static links can become inefficient with large load perturbations due primarily to impedance mismatch between the power receiver and the non-linear power recovery chain. As demonstrated below, an implant optimally matched for 1 mW achieves less than 5% efficiency when operated at 10 μW. Low efficiency is a major reliability problem, leading to significantly reduced battery life of the external source and potential loss of function of the IMD if the required power cannot be achieved. Therefore, an ideal power receiver should be tunable, along with the source, to maximize the power matching efficiency over a wide variety of applications and dynamic loads.

With proper choices of material and dimensions, a piezoelectric ultrasonic receiver can be designed to be mm-sized with an optimal electrical impedance for a highly variable load. In addition, by using frequency as a degree of freedom, we demonstrate off-resonance operation to modulate the receiver impedance for adaptive matching. In contrast, mm-sized implantable antennas, which are typically operated in the low-GHz range to combat tissue loss, offer much smaller radiation resistance and efficiency, due to mismatch in aperture and wavelengths as well as dielectric loading.

In this section, we first introduce the implant power recovery chain for an IMD, and describe the impedance match interface between the piezoelectric receiver and implant loads. We consider the effect of average $P_{load}$ on the input impedance of the power recovery circuit and demonstrate the concept of off-resonance operation for adaptable impedance tuning. Then a design procedure is presented to achieve the impedance specifications with a piezoelectric receiver. The selection of material and dimensions for ultrasonic receivers greatly influences frequency of operation and the impedance tuning range, so several different materials, including bio-compatible options, are compared. Finally, we use two adaptive matching topology examples to show significant improvement in the total implant efficiency over a non-tunable power recovery chain.

B2) Power Recovery Chain Under a Variable Load

Figure 8:
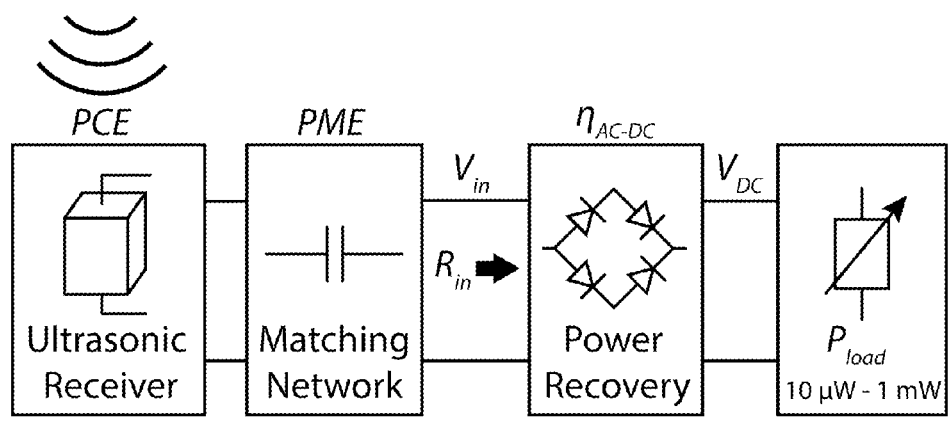
FIG. 8 is a schematic diagram of an ultrasonic power recovery chain. An effective load impedance, $R_{in}$, models the non-linear power recovery circuits, along with the implant power load, $P_{load}$.

A schematic diagram of an ultrasonic power recovery chain for an IMD in the steady state is shown in FIG. 8, which includes a piezoelectric receiver, a matching network, power recovery circuits, and an average application load. The total implant efficiency ($\eta_{implant}$) is determined by three major components: the acoustic-to-electrical power conversion efficiency of the receiver (PCE), the efficiency of the power recovery circuit ($\eta_{AC-DC}$) and the power matching efficiency (PME) between the first two components. Therefore, $\eta_{implant}$ can be represented as $$\eta_{implant} = \frac{P_{load}}{P_{acou}} = PCE \cdot PME \cdot \eta_{AC-DC}, \quad (1)$$

where $P_{acou}$ is the total incident acoustic power on top of the receiver. There is extensive literature on designing power electronics for power receivers to achieve high $\eta_{AC-DC}$; hence we focus on optimizing efficiency of the ultrasonic receiver and impedance matching interface due to the large variation of $P_{load}$ in an IMD.

A first-order calculation can be made to model any non-linear power recovery circuits, along with the implant load, as an effective average load impedance ($R_{in}$) annotated in FIG. 8 using the following equation:

$$R_{in} \simeq \frac{V_{in}^2}{2P_{load}} \eta_{AC-DC}, \quad (2)$$

where $V_{in}$ is the peak input rectified voltage. As a first-order estimation, when assuming a peak input of 2 V and $\eta_{AC-DC}$ of ~80%, the effective resistance can be computed from (2) to be between ~200 kΩ and ~2 kΩ for 10 μW to 1 mW load powers. An input voltage of 2V is assumed since it is much greater than typical CMOS thresholds, allowing for high $\eta_{AC-DC}$ (>80%) while also remaining below typical CMOS technology voltage limits. This calculation and the approximations are sufficient for our purpose of getting a first-order estimate of the effective implant load since modest differences do not greatly influence the PME and further refinements can be made using circuit simulators.

Figure 9:
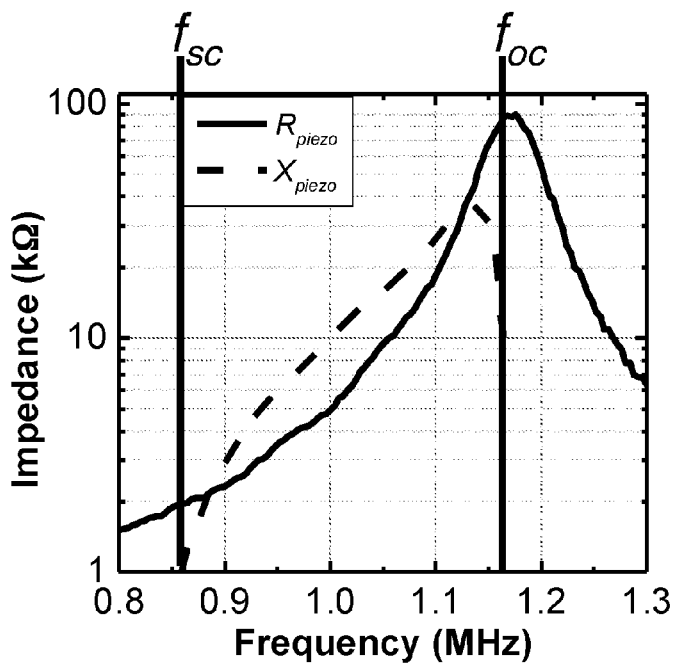
FIG. 9 is an impedance plot of a 1.5 mm×1.1 mm×1.1 mm ultrasonic receiver made from PZT5H measured with an impedance analyzer (Agilent 4294A).

In order to achieve a high PME over the wide range of $R_{in}$, a power receiver should exhibit a similar impedance range as $R_{in}$. FIG. 9 shows an example measured impedance profile of a mm-sized ultrasonic receiver made from Lead Zirconate Titanate 5H (PZT5H), a piezoelectric material, with dimensions of 1.5 mm×1.1 mm×1.1 mm. As seen in the figure, there is nearly two orders of magnitude change in the real part of the impedance ($R_{piezo}$) between the short-circuit ($f_{sc}$) and open-circuit ($f_{oc}$) resonances. The large value and range of $R_{piezo}$ offers a significant advantage for powering various $P_{load}$. With the appropriate design methodology to choose material and dimensions of the ultrasonic receiver, $R_{piezo}$ can be tuned to match the targeted $R_{in}$ range. Furthermore, we can leverage the inherent inductive nature of a piezoelectric receiver operating around mechanical resonance, in a band hereinafter referred to as the inductive band (IB), for impedance matching to obtain high PME. Conventionally, passive reactive components are used in order to perform impedance matching. Though large inductance around MHz is not practical when the form factor of implantable device is limited to mm-dimensions, capacitance is easy to obtain in a small volume or even on chip. The large inductive reactance with a reasonable quality factor in the IB, allows for impedance transformation with purely capacitive matching networks. Depending on the operating frequency and the topology of the matching network, the required matching capacitance ranges only from ~1 pF to 40 pF. The details of the matching network design will be described in section B5.

B3) Ultrasonic Receiver Design for IMDs

In this section, we focus on how to obtain the impedance behavior discussed in Section B2 by introducing a first-order circuit model that aids with the design process. The model provides sufficient accuracy for capturing the frequency behavior of the impedance and the radiation resistance of the piezoelectric receivers.

B3a) Ultrasonic Receiver Modeling

Figure 10:
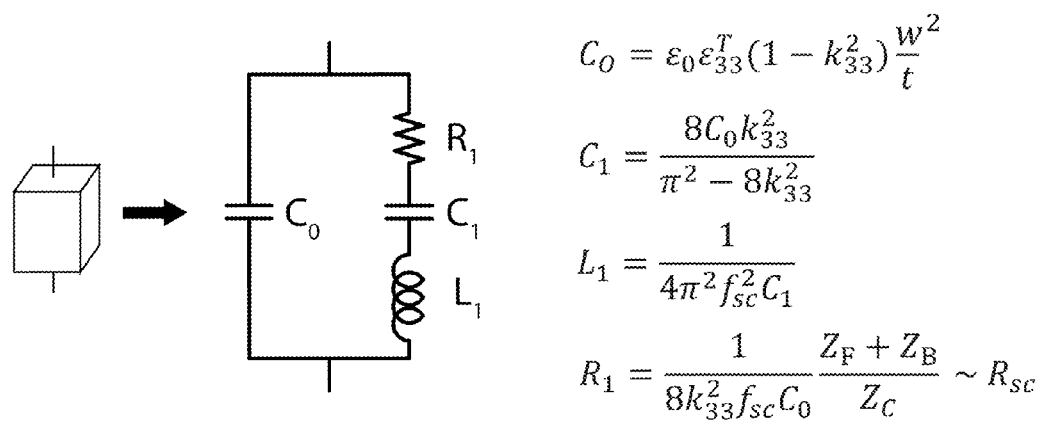
FIG. 10 is a schematic diagram of the one-dimensional series circuit model around fundamental resonance. The circuit elements are functions of material constants with length expander mode and dimensions as shown in the equations.

We use the one-dimensional series circuit model shown in FIG. 10 for first-order design of the piezoelectric receivers around fundamental resonance. The model has a series RLC tank with the intrinsic capacitance of the device ($C_0$) in shunt. The circuit element values are determined by width (w) and thickness (t) of the device, the piezoelectric material properties: relative permittivity ($\varepsilon^T$), electrical-mechanical coupling constant ($k_{33}$), acoustic impedance of the material ($Z_C$), front acoustic loading ($Z_F$), and back acoustic loading ($Z_B$). The model is more accurate when $Z_F$, $Z_B \ll Z_C$. This condition is satisfied in the design as the front of the device is loaded by tissue ($Z_{tissue} \simeq 1.4$-1.6 MRayls) when implanted in the body, and the receiver is designed with air backing ($Z_{air} \simeq 400$ Rayls) to minimize the effect of mechanical damping. Using this model, we investigate four different materials, PZT4, PZT5H, Barium Titanate (BaTiO$_3$), and Lithium Niobate (LiNbO$_3$), and compare their performances as ultrasonic receivers for IMDs. PZT4 and PZT5H are common piezoelectric materials widely utilized in imaging and sensor transducers. BaTiO$_3$ and LiNbO$_3$ are lead-free piezoelectric materials and are potentially biocompatible. The material properties, assuming length-expander bar mode (LE mode) operation, are listed in Table I. LE mode is utilized here as it provides better approximation when the aspect ratio of the receivers (G=w/t) is constrained below unity in order to reduce the overall implant volume.

TABLE I

Material properties for length expander bar mode

|  | PZT4 | PZT5H | BaTiO$_3$ | LiNbO$_3$ |
| --- | --- | --- | --- | --- |
| Density, ρ (kg/cm3) | 7500 | 7500 | 5700 | 4640 |
| Sound velocity, v (m/s) | 4100 | 3850 | 5000 | 6400 |
| Acoustic impedance, $Z_C$ (MRayl) | 30.8 | 28.9 | 28.5 | 29.7 |
| Electro-mechanical coupling coefficient $k_{33}$ | 0.70 | 0.75 | 0.5 | ~0.5 |
| Relative Permittivity $\varepsilon^T$ | 1300 | 3400 | 1700 | 30 |
| Mechanical Quality Factor | 500 | 65 | 300 | >1000 |

B3b) Selection of Dimensions and Materials for Receiver

The thickness of the receivers, t, and the sound velocity of the piezoelectric materials, v, are the main parameters for positioning the fundamental resonance. The $f_{oc}$ and $f_{sc}$ for G≪1 are given as, $$f_{oc} = \frac{v}{2t}, \quad (3)$$

$$f_{sc} \simeq \sqrt{1 + \frac{8k_{33}^2}{\pi^2}} f_{oc}, \quad (4)$$

where $f_{sc}$ is lower in frequency than $f_{oc}$, and they are related by $k_{33}$, which in turn determines the span of the IB. The resonance frequencies are inversely proportional to thickness of the material; thus, thinner devices have higher operating frequency. Due to mode coupling from finite width, the fundamental resonances will shift to slightly lower values for a practical aspect ratio. A correction factor of 1 to 0.7 for G≤1 can be inserted into (3) and (4) for more accurate determination of resonances. Nonetheless, this small shift does not have significant impact on the design process.

We aim to operate the devices with an IB between ~1-2 MHz as a trade-off between acoustic propagation losses through soft tissue (~1 dB·MHz/cm) and overall implant thickness. Based on (3), (4), and the material velocities listed in Table I, we can position the IB sufficiently close to the target range for all four materials using a thickness of 1.5 mm. Table II shows the calculated 1-D resonance frequencies for different materials. Receivers made from PZT4 and PZT5H have lower resonance frequencies than those made from BaTiO$_3$ and LiNbO$_3$ due to lower sound velocity.

TABLE II

Calculated resonance and impedance assuming

|  | PZT4 | PZT5H | BaTiO$_3$ | LiNbO$_3$ |
| --- | --- | --- | --- | --- |
| $f_{sc}$ (MHz) | 1.06 | 0.95 | 1.49 | 1.90 |
| $R_{sc}$ (kΩ) | 2.48 | 1.15 | 1.94 | 82.5 |
| $f_{oc}$ (MHz) | 1.37 | 1.28 | 1.67 | 2.13 |
| $R_{oc}$ (kΩ) | 244 | 119 | 56.6 | 2612 | t=1.5 mm, w=1.1 mm, $Z_F$=1.5 MRayls and $Z_B$~0 MRayls.

The area of the ultrasonic receiver and piezoelectric materials offers another trade-off between implant size and power capture area. As an example demonstration, we choose a lateral dimension, w, of 1.1 mm and use material as a design parameter to achieve the desired impedance range. Shown in FIG. 9, the off-resonance resistance in the IB is bounded by short circuit resistance, $R_{sc}$, and open circuit resistance, $R_{oc}$. Using the chosen dimensions, acoustic loadings, and the material properties in Table I, $R_{sc}$ and $R_{oc}$ can be calculated with the following equations derived from the series circuit model, $$R_{sc} \cong \frac{1}{8k_{33}^2 f_{sc} C_0} \frac{Z_F + Z_B}{Z_c} \propto \frac{1}{\rho v^2 \varepsilon^T k_{33}^2 (1-k_{33}^2)^{\frac{3}{2}}} \frac{t^2}{w^2} \quad (5)$$

$$R_{sc} \cong \frac{2k_{33}^2 f_{sc}}{\pi^2 f_{oc}^2 C_0} \frac{Z_c}{Z_F + Z_B} \propto \frac{\rho k_{33}^2}{\varepsilon^T (1-k_{33}^2)^{\frac{1}{2}}} \frac{t^2}{w^2}. \quad (6)$$

Equations (5) and (6) also show the direct relationship of $R_{sc}$ and $R_{oc}$ to the material properties under the assumption of given acoustic loadings (i.e. tissue and air for front and backing loading respectively). The calculated values for a thickness of 1.5 mm and width of 1.1 mm are shown in Table II. $R_{sc}$ and $R_{oc}$ are similar for receivers made from PZT4, PZT5H, and $BaTiO_3$; in addition, these materials offer an off-resonance resistance range that is well-matched to the desired $R_{in}$ from Section B2. Conversely, the resistances for receivers made from $LiNbO_3$ are nearly two orders of magnitude higher due to drastically lower relative permittivity as captured by (5) and (6). Although increasing the area of the piezoelectric receivers can be used to lower impedance range, this is undesirable for the purpose of miniaturization. Therefore, $LiNbO_3$ is not a preferred material for mm-sized implants of the specific targeted power range in this work, while PZT4, PZT5H, and $BaTiO_3$ are well-suited for our applications.

The above arguments are not meant to be a comprehensive analysis of all piezoelectric materials and sizing, but are provided to demonstrate various tradeoffs given a target power level and volume. Depending on the requirements of the application, a similar analysis can be carried out to investigate the feasibility of different materials and dimensions. For example, with the given dimensions, single crystalline piezoelectric materials such as PMN-PT (Lead Magnesium Niobate-Lead Titanate) are more suitable for applications requiring a higher power range (>1 mW) due to their large $\varepsilon^T$ (~5000) and $k_{33}$ (~0.9). One can also tune the properties of the piezoelectric materials by utilizing a composite piezoelectric transducer. Additionally, for shallow IMDs (<5 cm), a shorter link reduces the acoustic loss through tissue, and thus, higher frequency operation can be used to further scale down the thickness and width of the receiver while maintaining the desired impedance range.

B4) Characterization of Receivers

Ultrasonic receivers were built using PZT4, PZT5H, and $BaTiO_3$ to compare the general impedance behavior with the first-order analysis. We also measured acoustic-to-electrical power conversion efficiency, PCE, across the IB for each material. The PCE is defined mathematically as, $$PCE = \frac{P_{av,ele}}{P_{acou}} = \frac{P_{av,ele}}{I_0 A}, \quad (7)$$

where $P_{av,ele}$ is the available electrical power and $P_{acou}$ is the incident acoustic power, which is the product of incident acoustic intensity on top of the receiver characterized by a hydrophone, $I_0$, and physical area of the receiver, A. PCE is the acoustic-to-electrical efficiency analogue of aperture efficiency of an antenna. It varies across frequency and does not depend on electrical loading or characteristics of the ultrasonic transmitter so long as the receiver is in the far-field.

All piezoelectric receivers have a thickness of 1.5 mm, were diced to a width of 1.1 mm, and were packaged on top of a printed circuit board (PCB). We designed the package to minimize the total volume of the device. A bond wire and copper sheet were used to establish top and bottom electrical connections to receivers' electrodes. Air backing was created by sealing the via hole on the PCB. FIG. 11 shows the diagram and the photo of the package. Here 1102 is the piezoelectric receiver, 1104 is the copper sheet, and 1106 is the printed circuit board.

The receiver was immersed in a custom tank filled with mineral oil (1.16 MRayls) in order to minimize electrical parasitics and mimic the acoustic loading of body tissue. The ultrasonic transmitter (Olympus A303S) and the receiver were spaced at a distance of 6.0 cm to ensure both devices are in the far-field region. In practice, one would use a focusing array to get higher link efficiency, but here we are only interested in characterizing the ultrasonic receivers, independent of the transmitter.

B4a) Measured Resonances and Impedances of Receivers

Figure 12A:
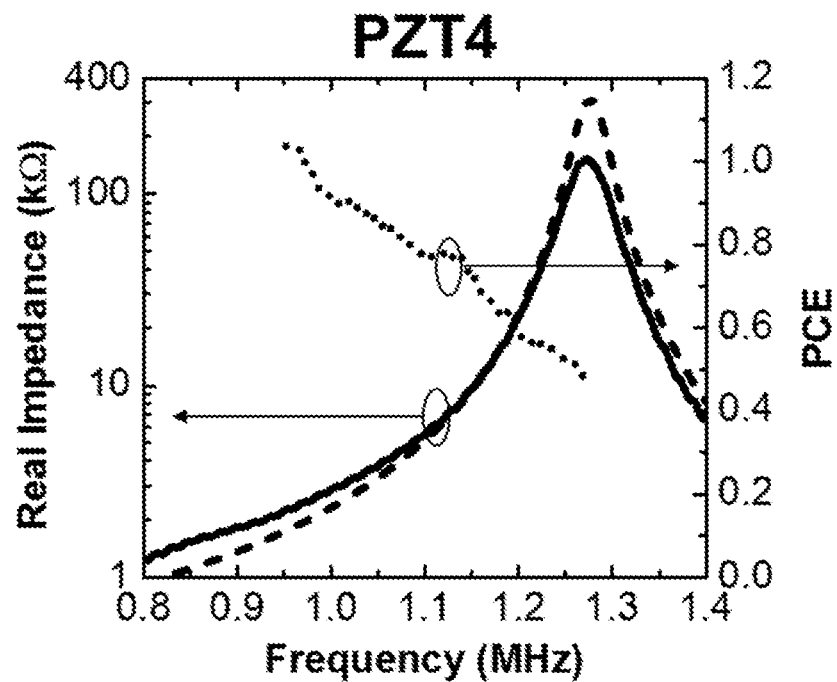
FIG. 12A shows the measured $R_{piezo}$ (solid line), the calculated $R_{piezo}$ from the series circuit model (dashed line), and the measured power conversion efficiency, PCE (dotted line), of the receiver made from PZT4.
Figure 12B:
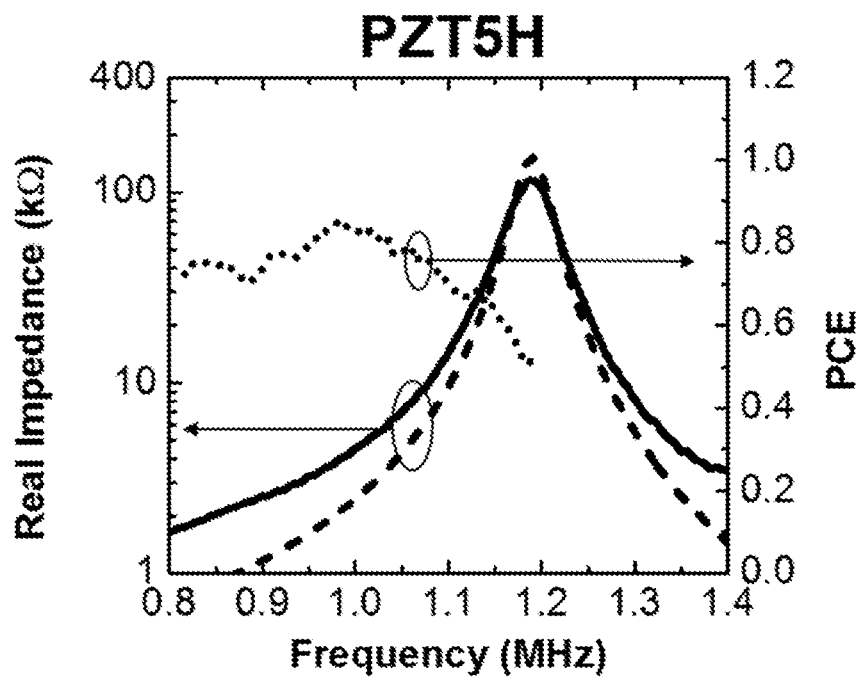
FIG. 12B shows the measured $R_{piezo}$ (solid line), the calculated $R_{piezo}$ from the series circuit model (dashed line), and the measured power conversion efficiency, PCE (dotted line), of the receiver made from PZT5H.
Figure 12C:
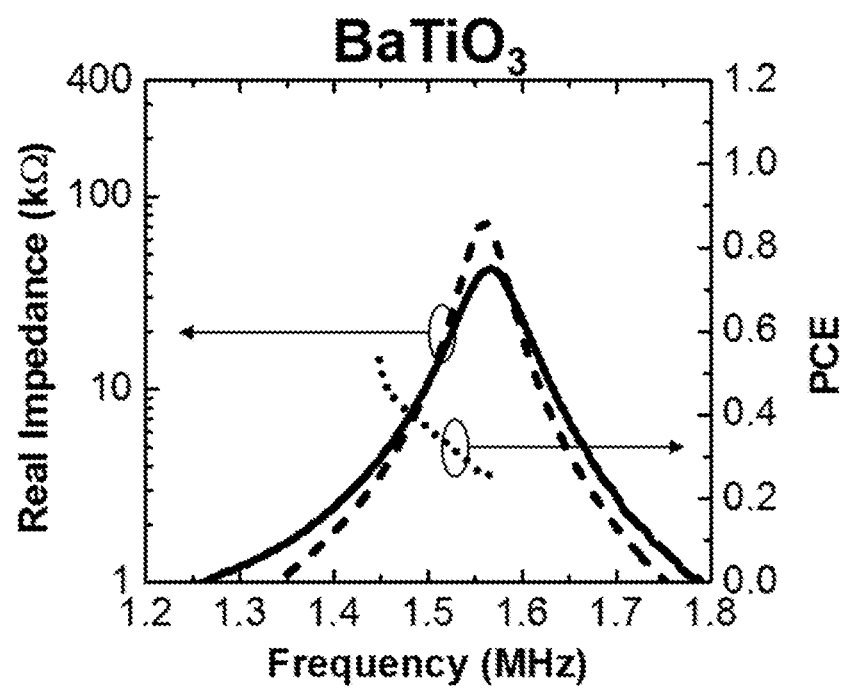
FIG. 12C shows the measured $R_{piezo}$ (solid line), the calculated $R_{piezo}$ from the series circuit model (dashed line), and the measured power conversion efficiency, PCE (dotted line), of the receiver made from $BaTiO_3$.

We characterized the impedance profile of the ultrasonic receivers using an impedance analyzer (Agilent 4294A). FIGS. 12A-C show the measured and calculated $R_{piezo}$ from the series circuit model with a correction factor of 0.93 (for G~0.7) to correct resonance frequency. The values of the resonance frequencies, $R_{sc}$, and $R_{oc}$ are listed in Table III. We omit the reactance across the IB since we can utilize a capacitor-only matching network to cancel the reactance as described in section B5. The measured $R_{piezo}$ curve (solid lines) has lower mechanical quality factor compared to the first-order model (dashed lines) since the model does not take into account the loss from material and package. Nonetheless, the range of measured $R_{piezo}$ agrees reasonably well with the first-order model. For each material, $R_{piezo}$ spans much of the ~2 kΩ to ~200 kΩ targeted range in the IB, suitable for IMDs. The measurement results demonstrate the utility of the series circuit model as a first-order design tool for IMD receivers.

TABLE III

Measured resonance frequencies and impedances

|  | PZT4 | PZT5H | $BaTiO_3$ |
|---|---|---|---|
| $f_{sc}$ (MHz) | 0.96 | 0.82 | 1.45 |
| $R_{sc}$ (kΩ) | 2.28 | 1.74 | 4.46 |
| $f_{oc}$ (MHz) | 1.27 | 1.19 | 1.58 |
| $R_{oc}$ (kΩ) | 154 | 120 | 40.2 |

B4b) Measured PCE of Receivers

PCE is computed from measured open circuit AC voltage across the terminals of the receiver along with the measured impedance for a given $I_0$. Measured PCE in the IB is also plotted in FIGS. 12A-C (dotted lines). Measurements for receivers of three different materials all present high PCE with variation across the entire IB. Similar to aperture efficiency for antenna, PCE larger than unity is possible for small resonators. As an example, even with a worst case PCE of 30%, we are still able to obtain 1 mW of time-averaged available power with less than 40% of the FDA limit (7.2 mW/mm$^2$). The PCE plots indicate that off-resonance operation can be utilized to transfer power efficiently for various $P_{load}$.

B5) Adaptive Matching to Maximize Efficiency

Figure 13:
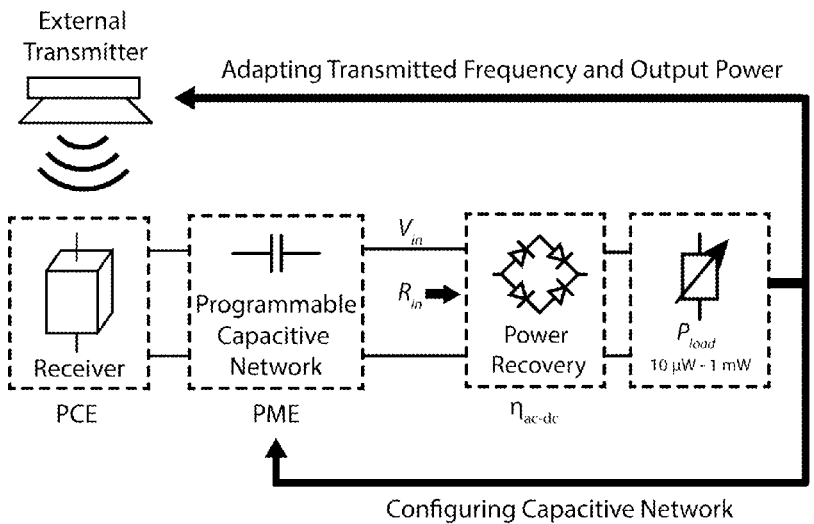
FIG. 13 is a conceptual diagram of a dynamic system with a programmable capacitive matching network and a closed-loop data link between IMDs and the external transmitter.

With the favorable impedance profile designed and measured in the previous sections, we now demonstrate how to operate these piezoelectric receivers efficiently for a dynamically varying $P_{load}$. The total implant efficiency, $\eta_{implant}$, from (1) is maximized by utilizing the full span of $R_{piezo}$ across the IB with capacitive-only matching networks. A truly dynamic design would implement a programmable capacitive matching network, such as switchable capacitor banks, to match the inductive reactance from the receiver at different operating frequencies. A closed-loop system with data uplink can be used to adaptively change the transmit frequency and acoustic intensity for various $P_{load}$. FIG. 13 shows a conceptual diagram of a closed-loop system with an adaptive power recovery chain.

Figure 14:
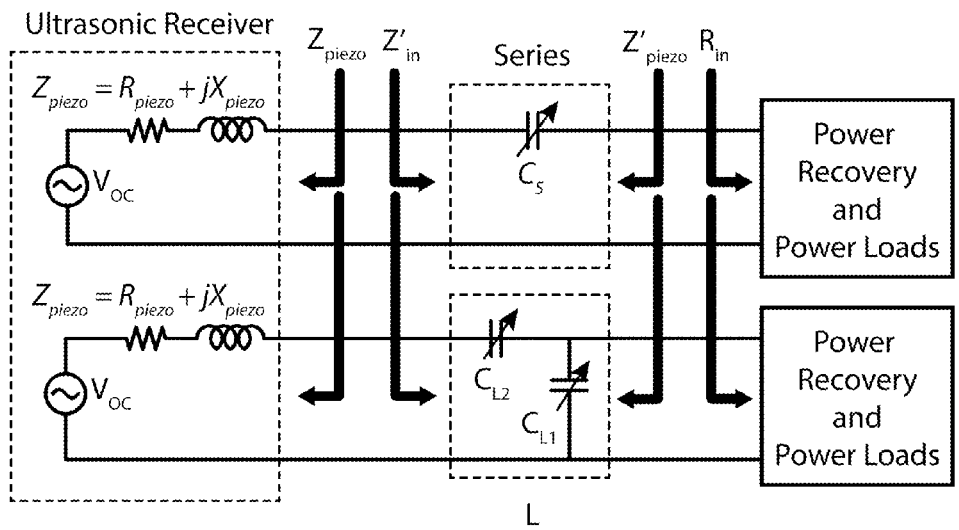
FIG. 14 is a schematic diagrams of the power recovery chain for off-resonance operation with series or L matching networks. The ultrasonic receiver is represented as a Thévenin's model. $Z'_{in}$ is the effective load impedance that the receiver sees before the matching network, and $Z'_{piezo}$ is the input impedance seen from the non-linear power recovery circuit and loads.

Series and L matching networks, shown in FIG. 14, can be used to increase $\eta_{implant}$. More complicated schemes can also be chosen for the same purpose. Measured characteristics of the PZT4 receiver in section B4 are used to illustrate the operation and efficiency gain of the two matching networks compared to a non-adaptive system. As seen in FIG. 14, the receiver is represented as a Thévenin model with an open circuit root-mean-squared voltage, $V_{oc}$, equal to $\sqrt{4P_{av,ele}R_{piezo}}$. A commercial full-wave bridge rectifier is selected as an example of the power recovery circuit in the power recovery chain in FIG. 8. Due to the nonlinearity in the power recovery circuit, a more accurate characterization of $R_{in}$ looking into the rectifier and load requires an iterative approach. Therefore, circuit simulations were performed using Keysight Advanced Design System (ADS) to obtain the optimal adaptive matching parameters at various load powers. In the simulations, output voltage is constrained to be 2 V and different load resistors are used to model different $P_{load}$. Measurements on matching networks are also performed to verify the simulation results using the same components.

B5a) Series Matching Network

The top part of FIG. 7 shows a series matching network, the simplest implementation of a programmable matching network. In order to maximize PME, $Z'_{piezo}$ and $R_{in}$ after the series matching network, or equivalently, $Z_{piezo}$ and $Z'_{in}$ before the matching network must be complex conjugate pairs respectively. A series matching network can be easily understood as matching $Z'_{piezo}$ to $R_{in}$. As $P_{load}$ varies, the operating frequency is selected such that $R_{piezo}$ is close to $R_{in}$. The series capacitor, $C_s$, is then configured to cancel out the remaining inductive part of the receiver, making $Z'_{piezo}$ matched to $R_{in}$. The series matching network is most effective when the range of $R_{piezo}$ in the IB is large enough to cover all possible $R_{in}$.

Figure 15A:
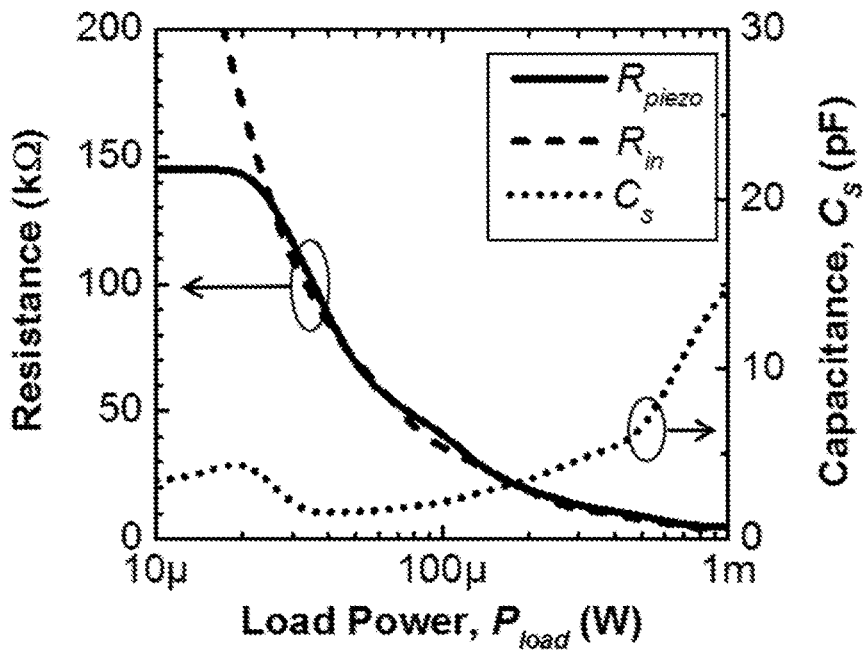
FIG. 15A shows simulated values of $R_{piezo}$ (solid line), required $R_{in}$ (dashed line) for optimal matching and capacitance, $C_s$ (dotted line), as a function of $P_{load}$ using the series matching network with the PZT4 receiver of section B4.
Figure 15B:
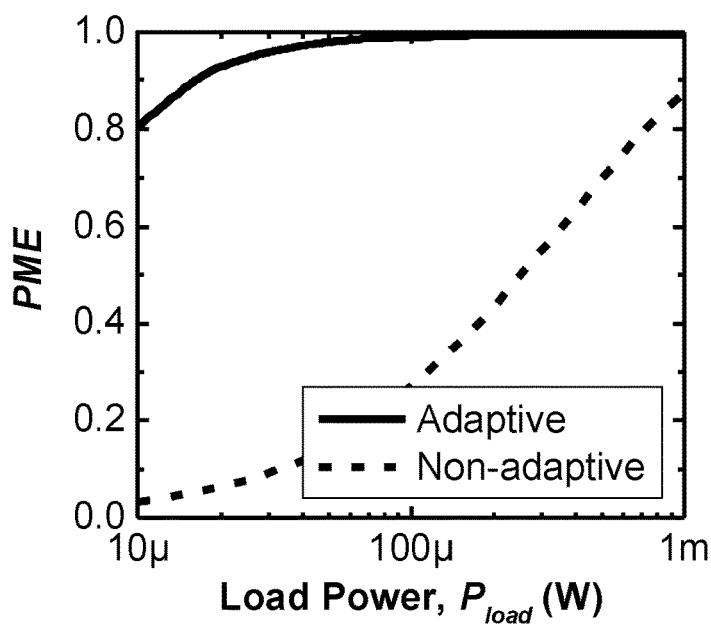
FIG. 15B shows optimized PME with adaptive matching (solid line) and the PME without adaptive matching (dashed line) versus $P_{load}$.

FIG. 15A shows the simulated values of $R_{piezo}$ and $R_{in}$ for optimal impedance matching as a function of $P_{load}$ from 10 µW to 1 mW. As anticipated from (2), $R_{piezo}$ follows $R_{in}$ and moves inversely with $P_{load}$. The range of $R_{piezo}$ limits the load power for which optimal matching can be obtained. For $P_{load}$ lower than 25 µW, required $R_{in}$ becomes too large to be matched by $R_{piezo}$ in the IB of the receivers; as a result, the optimal operating frequency stays at $f_{oc}$, and the PME drops. The capacitance values used for $C_s$, also shown in FIG. 15A, range from 1 pF to ~15 pF, which is easily achieved using on-chip capacitors for miniaturization. FIG. 15B shows the comparison of the PME between an adaptive system with a series matching network and a non-adaptive system. PME with series matching is able to reach almost 100% because of the presence of the tuned network. For the non-adaptive case, a static resonance frequency operation (at $f_{sc}$) is assumed; its PME drops significantly at lower load powers due to mismatch.

Figure 16:
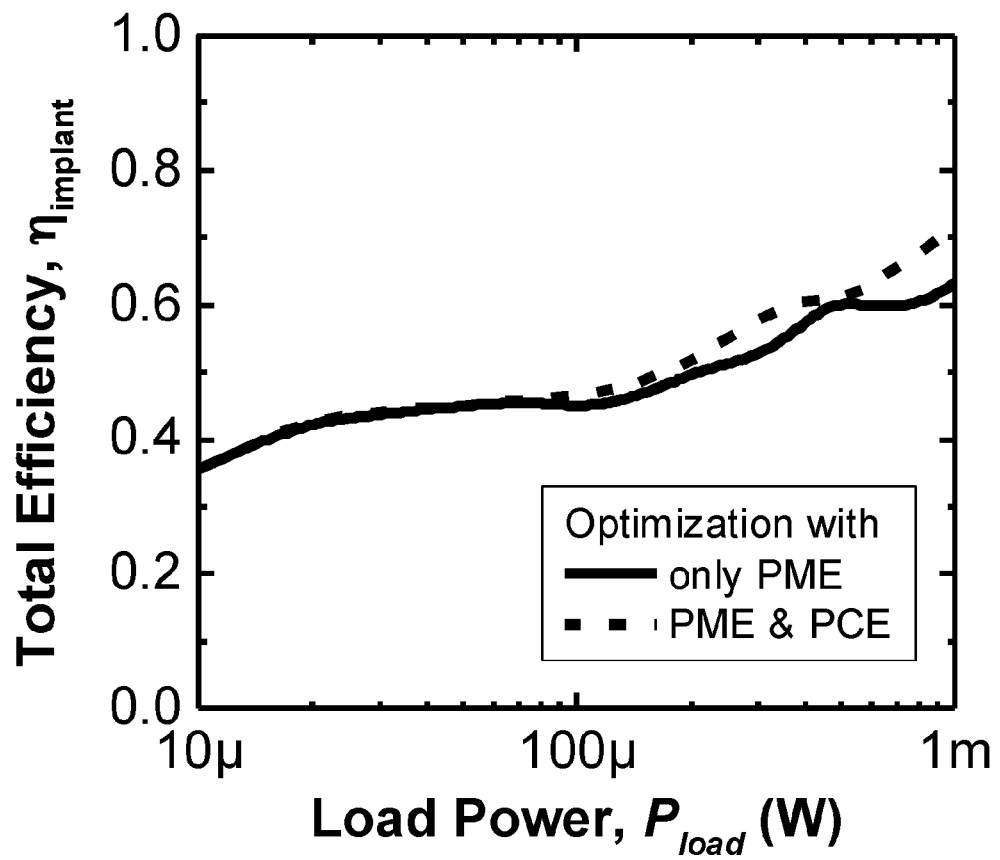
FIG. 16 shows simulated total implant efficiency calculated from (1) with optimization of only PME (solid line) and co-optimization considering both PME and PCE (dashed line).

The analysis so far has only considered $R_{piezo}$ and neglected the PCE, but the PCE could be taken into account since $\eta_{implant}$ is related to the product of PCE and PME by (1). FIG. 16 shows the simulated $\eta_{implant}$ of the power recovery chain including efficiency of the rectifier, $\eta_{AC-DC}$, when PCE is considered in the optimization process. Note that $\eta_{AC-DC}$ is about 80% over the entire range of load power. The result shows that co-optimizing PCE and PME together produces a higher $\eta_{implant}$ for some $P_{load}$. For the PZT4 receiver, the difference is most prominent at higher $P_{load}$, from 100 µW to 1 mW, with a boost of nearly 10 percentage points at 1 mW. Therefore, maintaining an operating frequency in a high PCE region but with a suboptimal PME can increase overall efficiency. This improvement is significant because at higher power levels, higher efficiency can reduce the required transmitted power.

B5b) L Matching Network

As seen in the comparison between simply maximizing PME and co-optimizing PME and PCE together, the efficiency for the co-optimized case is larger for some $P_{load}$. To decouple these two parameters, we can introduce an additional degree of freedom into the system, allowing for better optimization of $\eta_{implant}$.

An L matching network provides an additional degree of freedom with the extra shunt capacitor in the matching network. It can be used to transform the $R_{in}$ to a higher or lower value depending on the topology and quality factor of the matching network. Here, the network is designed to transform $R_{in}$ to match $R_{piezo}$ at the frequency where PCE is optimal—concurrently maximizing both PCE and PME. For the L matching network scheme shown in the bottom of FIG. 7, PME is maximized when $Z'_{in}$ is the complex conjugate of $Z_{piezo}$. $R_{in}$ is transformed down to a lower effective resistance by $C_{L1}$ to match $R_{piezo}$. $C_{L2}$ is then used to cancel out residual inductance from the piezoelectric receiver such that an optimal match is obtained. This transformation ratio is approximately bounded by the frequency dependent quality factor of the receiver, $Q_{piezo}$, defined as $Q_{piezo}=X_{piezo}/R_{piezo}$. The ratio is given as, $$\frac{R_{in}}{R_{piezo}} < 1 + Q_{piezo}^2. \qquad (8)$$

Figure 17A:
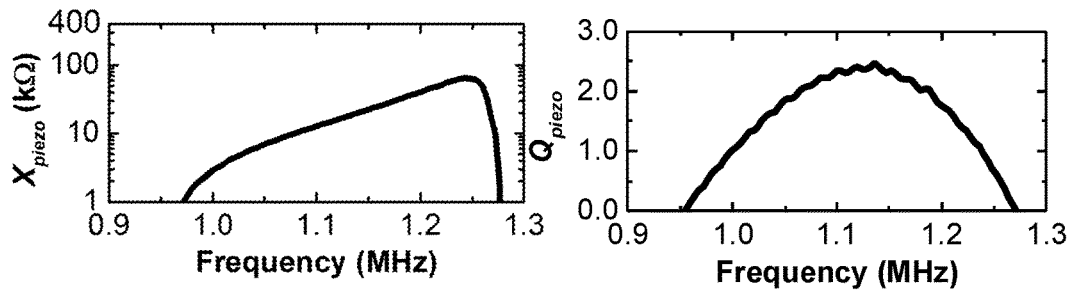
FIG. 17A shows measured $X_{piezo}$ and $Q_{piezo}$ of the PZT4 receiver.

A meaningful transformation ratio thus can be achieved with larger $Q_{piezo}$. From the series circuit model as well as impedance measurement of the receiver, it can be observed that materials with high $k_{33}$ result in higher $Q_{piezo}$ in the middle of the IB; therefore, using an L matching network is more advantageous for material with high $k_{33}$. FIG. 17A shows the measured reactance and $Q_{piezo}$ of the PZT4 receiver in the IB. A comparison of optimized $\eta_{implant}$ for L matching, series matching, and non-adaptive systems is plotted in FIG. 17B. An increase of as much as 20 percentage points in $\eta_{implant}$ is observed for the L matching network in comparison to series matching, while a nearly 50 percentage point efficiency boost is obtainable compared to a non-adaptive system operating at $f_{sc}$. The capacitances used in the network are about 2 pF to ~20 pF. Depending on the characteristics of the receiver, one can choose the appropriate matching networks to increase the total implant efficiency.

B5c) Measurement with Two Matching Networks

Figure 17B:
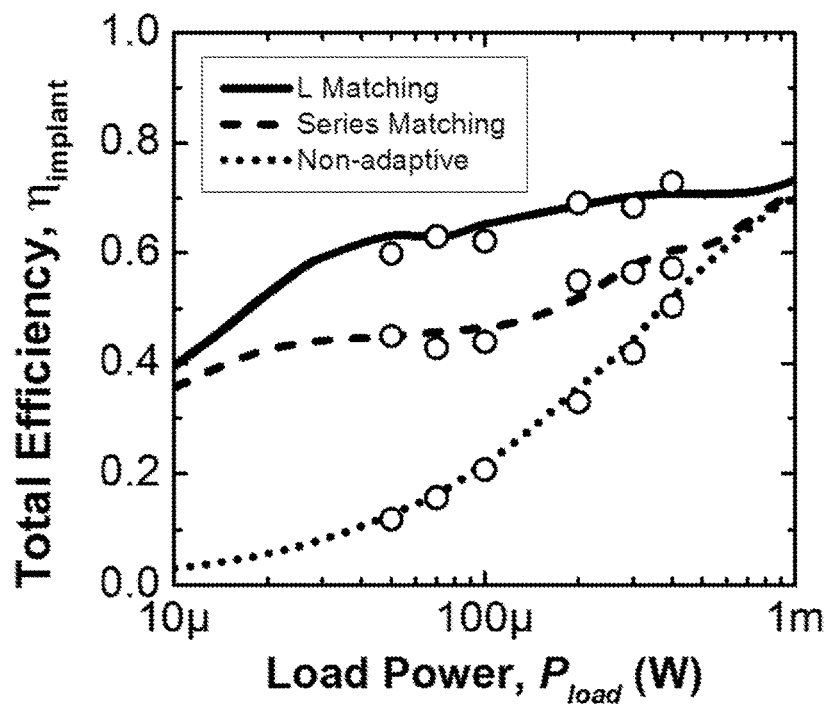
FIG. 17B is a comparison of $\eta_{implant}$ from simulation of system using the L matching network (solid line), series matching network (dashed line), and non-adaptive system (dotted line). A boost in efficiency is observed throughout the relevant range of $P_{load}$. Measurements at six different $P_{load}$ are represented by circles. ADS simulation and measurement are in good agreement.

We performed wireless power transfer measurements for the power recovery chain at various load powers to verify the results obtained from ADS simulations for both matching networks. A full-wave bridge rectifier (same as the one used in simulation) and discrete capacitors for implementing matching networks are added onto the PCB board. Both the rectifier and programmable capacitors can be designed on-chip for further miniaturization. Different load resistors modeling $P_{load}$ are connected off the board. The DC output voltage of the rectifier is measured through an oscilloscope. Measured efficiency at six different $P_{load}$ for the three different configurations are shown in FIG. 17B in circles. The measurement results are in good agreement with simulation, demonstrating the capability of using matching networks for efficient power transfer.

B6) Conclusion

We utilize off-resonance operation of mm-sized ultrasonic receivers to maximize power transfer efficiency of IMDs with a wide range of power levels. The piezoelectric receivers are designed to meet mm-dimensional requirements while also achieving a favorable impedance range for efficient power delivery. Materials and dimensions are identified as two of the major design variables to obtain the desired impedance range for typical implant applications. Theoretical analysis and experimental verification were performed to compare the performance of several different materials—PZT4, PZT5H, and $BaTiO_3$ were concluded to be well-suited for IMD powering and achieve high PCE. Using a capacitive-only matching network, $\eta_{implant}$ for various load powers can be maximized by utilizing the inductive band impedance of the receiver, and thus avoiding the use of conventional bulky inductors. Both series and L matching networks are analyzed and compared to typical resonance-based operation. The simulation and measurement results show significant increases in the total implant efficiency for a miniaturized implant with an ultrasonic receiver and a proper matching network.

The invention claimed is:

1. A system for providing power to an implanted receiver, the system comprising:
   1) an acoustic transmitter configured to provide acoustic radiation having an acoustic frequency f;
   2) a receiver unit configured to be implanted into a biological subject, wherein the receiver unit is configured to receive the acoustic radiation and to be powered by the acoustic radiation;
   wherein the receiver unit comprises
   i) an acoustic transducer configured to receive the acoustic radiation and to provide an input electrical AC signal;
   ii) an adaptively reconfigurable electrical impedance matching network configured to receive the input electrical AC signal and to provide an output electrical AC signal, wherein the electrical impedance matching network is capacitive without including any inductors;
   iii) an electrical load; and
   iv) a power recovery circuit configured to receive the output electrical AC signal and to provide DC power to the electrical load; and
   3) a system controller;
   wherein the system controller is configured to
   a) alter one or more controlled system parameters including the acoustic frequency f, and
   b) alter a configuration of the adaptively reconfigurable electrical impedance matching network,
   responsive to changes in one or more system variables to control power delivery from the acoustic transmitter to the electrical load.

2. The system of claim 1, wherein the acoustic transducer has an inductive band, and wherein the acoustic frequency is controlled by the system controller such that the acoustic frequency is within the inductive band.

3. The system of claim 1, wherein the acoustic frequency is controlled by the system controller such that the acoustic transducer impedance is tuned to match an impedance as seen at an input of the adaptively reconfigurable electrical impedance matching network for the electrical load.

4. The system of claim 1, wherein the acoustic transmitter is configured to provide continuous acoustic radiation, and wherein the acoustic frequency is varied continuously by the system controller.

5. The system of claim 1, wherein the acoustic transmitter is configured to provide pulsed acoustic radiation, and wherein the acoustic frequency is varied from pulse to pulse and/or varied within pulses by the system controller.

6. The system of claim 1, wherein the controlled system parameters further include one or more parameters selected from the group consisting of: power from the acoustic transmitter, beam pattern of the acoustic radiation, phase of the acoustic radiation, pulse duration of the acoustic radiation, and duty cycle of the acoustic radiation.

7. The system of claim 1, wherein the one or more system variables are selected from the group consisting of: load impedance, acoustic transmitter efficiency, acoustic transmitter impedance, acoustic transmitter beam pattern, distance between the acoustic transmitter and the receiver unit, transmission efficiency between the acoustic transmitter and the receiver unit, receiver unit efficiency, receiver unit impedance, receiver unit aperture, changes in parameters of the power recovery circuit, and changes in parameters of the adaptively reconfigurable electrical impedance matching network.

8. The system of claim 1, wherein the power recovery circuit is adaptively reconfigurable responsive to changes in the one or more system parameters.

9. The system of claim 1, wherein the electrical load provides one or more functions selected from the group consisting of: electrical stimulation, optical stimulation, acoustic stimulation, neural recording, temperature sensing, pressure sensing, drug sensing, impedance sensing, detecting biological species, heating, and data communication.

10. The system of claim 1, wherein the system controller includes one or more system sensors selected from the group consisting of: load power sensor, load voltage sensor, load current sensor, output electrical AC signal voltage sensor, transducer output impedance sensor, transducer output voltage sensor, transducer output current sensor, receiver unit temperature sensor, and acoustic transmitter temperature sensor.

11. The system of claim 1, wherein the electrical load is an energy storage device.

12. The system of claim 1, wherein the system controller is configured to provide location tracking of the receiver unit combined with beam forming of the acoustic radiation according to the tracked location of the receiver unit.

13. The system of claim 1, wherein the receiver unit further comprises one or more auxiliary acoustic transducers, wherein an output of the acoustic transducer and outputs of the one or more auxiliary acoustic transducers are combined and provided to the electrical load.

14. The system of claim 13, wherein the output of the acoustic transducer and the outputs of the one or more auxiliary acoustic transducers are combined coherently.

15. The system of claim 13, wherein the output of the acoustic transducer and the outputs of the one or more auxiliary acoustic transducers are combined incoherently.

16. The system of claim 13, wherein the controlled system parameters further include a combining configuration of the acoustic transducer and the one or more auxiliary acoustic transducers.

17. The system of claim 1, wherein the acoustic transmitter is configured to be wearable.

18. The system of claim 17, further comprising a mobile device in communication with the acoustic transmitter.

19. The system of claim 1, wherein the receiver unit further comprises at least a back-side structure having acoustic impedance of 10 Mrayl or less.

20. The system of claim 19, wherein the back-side structure has an acoustic impedance of 2 Mrayl or less.

21. The system of claim 1, wherein the system controller is configured to provide real-time control of the controlled system parameters.

22. The system of claim 1, wherein the system controller is configured to provide pre-determined changes to the controlled system parameters.

* * * * *